United States Patent [19]

Montag et al.

[11] Patent Number: 5,104,845

[45] Date of Patent: Apr. 14, 1992

[54] GROUP 1 METALLOALUMINUM BORATES

[75] Inventors: Ruth A. Montag, Naperville; Larry C. Satek, Wheaton, both of Ill.

[73] Assignee: Amoco Corporation, Chicago, Ill.

[21] Appl. No.: 247,614

[22] Filed: Sep. 22, 1988

[51] Int. Cl.$^5$ .......................... B01J 21/02; C01B 35/10
[52] U.S. Cl. ..................................... 502/202; 423/277; 502/300; 502/344; 502/355
[58] Field of Search ................ 423/277; 502/300, 344, 502/355, 202

[56] References Cited

U.S. PATENT DOCUMENTS 3,860,692  1/1975  Nies et al. ............................ 423/277

OTHER PUBLICATIONS

Chemical Abstracts, vol. 100, No. 2, 1984, p. 416, Abs. No. 13283c, Kozhina, I. I.; Karnilova, E. E.; Petroskii, G. T.; "X-Ray Diffraction Study of the Potassium Oxide-Aluminum Oxide-Boron Oxide System".

Primary Examiner—Jose G. Dees
Assistant Examiner—Porfirio Nazario
Attorney, Agent, or Firm—Fred S. Jerome; William H. Magidson; Ralph C. Medhurst

[57] ABSTRACT

The preparation, structure, and properties of solid inorganic materials containing aluminum, boron, oxygen and at least one metallo element selected from Group IA of the Periodic Table is described. Also described is the use of such materials in catalytic compositions for the conversion of organic compounds. In particular, the new materials having the general formula:

$$(x)\ M_2O \cdot (y)\ Al_2O_3 \cdot (z)\ B_2O_3$$

where M is at least one metallo element selected from Group IA of the Periodic Table having atomic number from 11 through 55, inclusive, and x, y and z are numbers representing molar amounts of the oxides are described as well as the use of such materials in various catalyzed processes including synthesis of methacrylic acid.

7 Claims, No Drawings

GROUP 1 METALLOALUMINUM BORATES

The preparation, structure, and properties of solid inorganic materials containing aluminum, boron, oxygen and at least one metallo element selected from Group IA of the Periodic Table are described. Also described is the use of such materials in catalytic compositions for the conversion of organic compounds. In particular, the new materials having the general formula:

$$(x)M_2O\cdot(y)Al_2O_3\cdot(z)B_2O_3$$

where M is at least one metallo element selected from Group IA of the Periodic Table having atomic number from 11 through 55, inclusive, and x, y and z are numbers representing molar amounts of the oxides are described as well as the use of such materials in various catalyzed processes including synthesis of methacrylic acid.

The use of an active metallo element or a supported metallo element composition containing aluminum and boron as a conversion catalyst is known in the art U.S. Pat. No. 3,883,442 to McArthur is illustrative of prior art disclosing the superiority of a supported active metal catalyst to resist shrinkage at high temperatures (up to 1600° C.) by stabilization of a preformed alumina catalyst support McArthur states stabilization was achieved by impregnating an alumina support with a solution of a boron compound which is thermally decomposable to $B_2O_3$, followed by drying and calcining of the impregnated support at temperatures below about 1500° C., but sufficiently high to decompose the boron compound McArthur also discloses that the most commonly used technique of preparing a supported metallo element catalyst involved: following calcination, impregnating in conventional manner the alumina support material containing some retained $B_2O_3$ with a solution of the desired metal salt, preferably those that are thermally decomposable to give the corresponding metal oxides and/or sulfides, and calcining the salt-impregnated In U. S. Pat. No. 3,954,670 to Pine a boria-alumina based catalyst is disclosed in the combination of a metallo element selected from the group consisting of rare earth, Group IB, IIA, IIB, IIIB, IVA, IVB, VB, VIIB and VIII, and a boria-alumina catalyst support materials prepared by hydrolysis of a mixture of aluminum alkoxide and boron alkoxide in the presence of water at a temperature in the range of 20° to 100° C. The disclosed catalyst compositions, said to be useful for desulfurization, denitrogenation, reforming and other hydrocarbon conversion processes, included both cobalt and nickel as metallo elements in combinations with the boria-alumina catalyst composition disclosed in Pine and, optionally, a crystalline aluminosilicate zeolite with or without rare earth elements. However, Pine neither discloses nor suggests any mixed oxide composition of a Group IA metallo element, aluminum, and boron.

Zletz in U.S. Pat. No. 4,729,979, which is hereby incorporated by reference, discusses the characteristics of a good catalyst and/or catalyst support and a new crystalline copper aluminum borate characterized by a specific X-ray diffraction pattern, surface area and pore volume which is at least partially reducible with hydrogen at a temperature of no more than 350° C. to a composition containing zero valent copper and Al Satek in U.S. Pat. No. 4,590,324, which is hereby incorporated by reference, discusses using the new crystalline copper aluminum borate as a catalyst to dehydrogenate alkylaromatics to alkenylaromatics. Zletz et al. in U.S. Pat. No. 4,645,753, which is hereby incorporated by reference, discusses doping the new crystalline copper aluminum borate to contain an alkali metal or alkaline earth metal element for use as a catalyst to dehydrogenate alkylaromatics to alkenylaromatics. The Zletz, Satek, and Zletz et al. patents alone or in combination neither disclose nor suggest a mixed oxide composition of aluminum, boron, and a metallo element without copper. Furthermore, these patents disclose crystalline copper aluminum borate having significant X-ray diffraction lines which are substantially different from X-ray diffraction patterns for crystalline materials of the present invention.

Schwab and Bertaut disclose the preparation of a single crystal of a boroaluminate of nickel in *Bull. Soc. Fr. Mineral. Cristollogr.* (1970), 93, 255–257, "Structure di boroaluminate $B_2O_3\cdot Al_2O_3\cdot 4NiO$" which is hereby incorporated by reference, by mixing the oxides $B_2O_3$, $Al_2O_3$ and NiO in the mol ratio of 1:1:4 plus a large excess of $B_2O_3$ [sic], heating the mixture to 1300° C., cooling the hot mixture carefully to room temperature at a rate of 50° C. per hour, and treating the cooled product with dilute nitric acid to dissolve excess boria providing single crystals about 2–3 mm long. The atomic coordinates for a single crystal structure are reported, however no powder x-ray diffraction pattern is reported Boroaluminates of nickel produced by the indicated route are believed to be well-defined, dense crystalline particles which have an extremely low surface area due to heating a mixture of oxides to a temperature of 1300° C.

Unsaturated carboxylic acids such as methacrylic acid, and the esters of such acids such as methyl methacrylate, are widely used for the production of corresponding polymers, resins and the like. Typically, a saturated monocarboxylic acid, such as propionic acid (PA), can be catalytically reacted with formaldehyde (FA) to produce an alpha, beta-ethylenically unsaturated monocarboxylic acid, such as methacrylic acid (MA), and water as a co-product. The produced alpha, beta-ethylenically unsaturated monocarboxylic acid can be esterified to a polymerizable, alpha, beta-ethylenically unsaturated monocarboxylic acid ester, such as methyl methacrylate (MMA).

MMA is a monomer containing a carbon-carbon double bond (C=C) and a carbonyl group

Polymers derived from MMA are sometimes also referred to as "acrylic" or "acrylic-type" polymers The MMA-type polymers have desirable transparency, weatherability and physical strength properties Typical end-uses for MMA-derived polymers include acrylic sheet that can be fabricated into signs, advertising displays, lighting fixtures, glazing materials, structural panels and the like, molding resins for automobile, bus, truck and other vehicular tail-light lenses, plumbing and electrical fixtures and the like, as well as constituents of a variety of surface coatings, adhesives, inks, floor polishes and the like Generally, the condensation reaction to synthesize an alpha, beta-ethylenically unsaturated aliphatic monocarboxylic acid, such as MA, takes place in the vapor or gaseous phase and in the presence of a catalyst which can be basic, acidic, or substantially neutral. In the absence of the catalyst, reactants typically require addition of heat energy to overcome an "energy of activation" of the reaction, which can be a barrier to formation of the desired products Also, in the instance where the reactants are chemically converted to a variety of products, a catalyst may tend to increase the rate of formation of one product relative to one or more of the other products. Such a catalyst is said to possess increased selectivity qualities, often a consideration when choosing a catalyst for commercial production purposes Reaction temperature plays an important role in the activity of a catalyst, another important consideration. At a particular temperature, for example, a commercially acceptable percentage of the reactants might be converted to a desired product, with only a relatively minor percentage of the reactants being converted to undesired by-products. Typically, an increase in the temperature of the reaction not only tends to increase the rate at which the reactants are converted to the desired product or products, but also tends to increase the rate at which undesired by-products are produced as well.

Catalysts commonly used for reacting PA with FA to produce MA are alkali metals supported on silica. Typical catalysts of this type are disclosed in U.S. Pat. No. 4,567,030 to Yuasa et al., U.S. Pat. No. 4,147,718 to Gaenzler et al., U.S. Pat. No. 3,933,888 to Schlaefer, U.S. Pat. No. 3,840,587 to Pearson, U.S. Pat. No. 3,247,248 (see also Canadian Patent No. 721,773) to Sims et al., U.S. Pat. No. 3,840,588 to Pearson, and U.S. Pat. No. 3,014,958 to Koch et al.

These prior-art catalysts, while effecting condensation of PA with FA to produce MA, unfortunately also generate undesirable by-products that have to be separated from the produced MA. Relatively low conversion and/or selectivity performance values, together with relatively low catalyst useful-life values, are additional drawbacks.

Generally, when PA and FA are reacted in the vapor phase, and in the presence of a catalyst, to produce desired product MA and co-product $H_2O$, a variety of undesirable by-products are simultaneously produced as well. The more common of these undesirables are hereinafter referred to as by-product A (2,5-dimethyl-2-cyclopenten-1-one), by-product B (2,4,4-trimethyl-gammabutyrolactone), and by-product 3-P (3-pentanone). The presence of these by-products is generally undesirable because current MA-esterification and MMA-polymerization technology requires separation of these by-products either from the MA before it is esterified to MMA, or before the produced MMA is polymerized. It is additionally desirable to remove by-product A from the MA prior to esterification as the presence of this by-product tends to interfere with the desired formation of MMA. In particular, the presence of by-product A in the MA tends to cause an undesirable polymerization of MA and attendant separation problems. Loss of product also may become significant.

While reduction of reaction temperature tends to increase the useful life of the catalyst per se, a reduced operating temperature may reduce overall operating costs as an added benefit. The reduction in the amounts of the undesirable by-products, moreover, tends to reduce, and may even eliminate, the costs attendant to (1) the removal of the undesirable by-products from the MA prior to esterification, and (2) the purification of the MMA prior to polymerization.

Accordingly, it would be desirable to have a catalyst which decreases undesirable by-product generation without decreasing PA conversion or decreasing useful catalyst life.

The general object of the present invention is to provide a new composition useful as a catalyst to convert organic compounds to other compounds.

Another general object of this invention is to produce a new catalyst which is suitable for production of an alpha, beta-ethylenically unsaturated monocarboxylic acid by condensation of a saturated monocarboxylic acid with a source of formaldehyde.

Other objects and advantages of the invention will become apparent upon reading the following detailed description and appended claims.

SUMMARY OF THE INVENTION

In one aspect, the present invention is a solid material, suitable for production of an alpha, beta-ethylenically unsaturated monocarboxylic acid by condensation of a saturated monocarboxylic acid with a source of formaldehyde, which solid material consists essentially of aluminum, boron, oxygen and at least one metallo element selected from Group IA of the Periodic Table having an atomic number from 11 through 55, inclusive.

In another aspect, the invention describes the preparation and properties of a solid material consisting essentially of aluminum, boron, oxygen and at least one metallo element selected from Group IA of the periodic Table having an atomic number from 11 through 55, inclusive.

In a preferred embodiment the present invention is an amorphous solid material consisting essentially of aluminum, boron, oxygen and at least one metallo element selected from Group IA of the Periodic Table having an atomic number from 11 through 55, inclusive, and the amorphous solid material has a surface area of least 20 $m^2/g$.

In another preferred embodiment the present invention is a crystalline inorganic material comprising aluminum, boron, oxygen and at least one metallo element selected from Group IA of the Periodic Table having an atomic number from 11 through 55, inclusive, having an X-ray diffraction pattern comprising significant lines substantially as described in Table I.

TABLE I

| Principal XRD Lines | |
|---|---|
| Interplanar Spacing[1] d, Å | Assigned Strength[2] |
| 4.28 ± 0.3 | W |
| 4.23 ± 0.3 | W |
| 3.40 ± 0.3 | W |
| 3.01 ± 0.2 | VS |
| 2.66 ± 0.2 | W |
| 2.47 ± 0.2 | M |
| 2.37 ± 0.2 | W |
| 2.14 ± 0.1 | W |
| 2.13 ± 0.1 | W |
| 2.11 ± 0.1 | M |
| 1.51 ± 0.1 | W |

[1] Angstroms
[2] VW = very weak; W = weak; M = medium; S = strong; VS = very strong As is generally known, the assigned strengths in X-ray diffraction patterns may vary depending upon the characteristics of the sample. The observed line strength in any particular sample may vary from another sample. Also, X-ray diffraction lines of a particular crystalline material may be obscured by lines from other materials present in a measured sample.

In another aspect, the invention describes the preparation and properties of a solid inorganic material comprising crystalline $M_2Al_2B_2O_7$, where M is at least one metallo element selected from Group IA of the Periodic Table having an atomic number from 11 through 37, inclusive, and providing an X-ray pattern comprising the X-ray diffraction lines and assigned strengths shown in Table I.

In still another aspect, the invention describes the use of such solid materials in catalytic compositions for the conversion of organic compounds.

The heterogeneous catalysts of the present invention comprise mainly aluminum, boron, oxygen and at least one metallo element selected from Group IA of the periodic Table having an atomic number from 11 through 55, inclusive, in the +1 oxidation state and in an amount of about 1 to about 45 percent by weight, preferably in an amount of about 4 to about 35 percent by weight, and more preferably in an amount of about 7 to about 15 percent by weight, based on the weight of the catalyst. The present catalyst may also include a relatively small amount of other compounds which are amorphous or crystalline, such as amorphous aluminas or crystalline aluminum borates.

In a further aspect, the invention describes the use of such materials for production of an alpha, beta-ethylenically unsaturated monocarboxylic acid by condensation of a saturated monocarboxylic acid, such as propionic acid, with formaldehyde to produce an alpha, beta-ethylenically unsaturated monocarboxylic acid, such as methacrylic acid.

DETAILED DESCRIPTION OF THE INVENTION

The Group IA metallo element or elements, aluminum, boron, and oxygen solid materials of the present invention can be prepared by calcining a mixture of a source of at least one metallo element ion selected from the group consisting of sodium(I) ions, potassium(I) ions, rubidium(I) ions and cesium(I) ions, a source of alumina, and a source of boria.

Conditions of calcination include a temperature within the range of about 400° C. to about 1500° C., a pressure of at least about one atmosphere, and a reaction time that is sufficient to affect formation of a crystalline metalloaluminum borate. Increasing pressure and temperature of calcination generally effect formation of a crystalline metalloaluminum borate in a shorter reaction time. However, a high temperature of calcination typically results in crystalline materials with less desirable surface properties, for example low surface area. Preferred calcination temperatures are in a range of about 400° C. to 1100° C. Calcination can be carried out in air, nitrogen or other inert gases. A preferred atmosphere for calcination contains oxygen.

The solid materials of this invention can be prepared generally by dispersing the required ingredients in a liquid medium, preferably an aqueous medium, removing substantially all the liquid to form superficially dry mixture, and calcining the dry mixture.

The cesium compound, for purposes of the present invention, can be relatively volatile, water or solvent soluble, or thermally decomposable.

Illustrative of the thermally decomposable cesium compounds that can be utilized are cesium borofluoride ($CsBF_4$), cesium bromate ($CsBrO_3$), cesium bromochloride iodide (CsIBrCl), cesium dibromoiodide ($CsIBr_2$), cesium perchlorate ($CsClO_4$), cesium chloroiodide ($CsICl_2$), cesium dichloroiodide ($CsICl_2$), cesium hydride (CsH), cesium nitrate ($CsNO_3$), cesium oxide ($Cs_2O$), and the like.

Illustrative of the relatively volatile cesium compounds that can be utilized are cesium dibromochloride ($CsBr_2Cl$), cesium formate [$Cs(CHO_2 \cdot H_2O)$], cesium hydrofluoride (CsF·HF), cesium hydrogencarbide ($CsHC_2$), cesium hydroxide (CsOH), cesium pentaiodide ($CsI_5$), cesium triiodide ($CsI_3$), cesium hydrogen nitrate ($CsNO_3 \cdot NHO_3$), cesium dihydrogen nitrate ($CsNO_3 \cdot 2HNO_3$), cesium peroxide ($Cs_2O_2$), cesium trioxide ($Cs_2O_3$), cesium propionate [$Cs(C_3H_5O_2)$], and the like.

Illustrative of the water-soluble cesium compounds that can be utilized are cesium acetate [$Cs(C_2H_3O_2)$], cesium azide ($CsN_3$), cesium benzoate [$Cs(C_7H_5O_2)$], cesium monobromide (CsBr), cesium carbonate ($Cs_2CO_3$), cesium hydrogen chloride (CsCl), cesium flouride (CsF), cesium formate [$Cs(CHO_2)$], cesium hydroxide (CsOH), cesium iodide (CsI), cesium nitrate ($CsNO_3$), cesium oxalate [$Cs_2(C_2O_4)$], cesium salicylate [$Cs(C_7H_5O_3)$], cesium hydrogen tartrate [$CsH(C_4H_4O_6)$], and the like. The cesium compound can also be soluble in a water-miscible or water-immiscible organic solvent.

Specifically, the cesium compound is preferably selected from the group consisting of cesium carbonate, cesium hydroxide, cesium propionate, cesium fluoride and cesium nitrate, and more preferably is cesium carbonate or cesium propionate.

More particularly, the cesium is preferably contained in an aqueous solution of relatively high cesium concentration, usually approaching saturation for the particular compound that is utilized More dilute solutions can be used, if desired. When a liquid medium is used, the source of sodium(I) ions, potassium(I) ions, rubidium(I) ions and/or cesium(I) ions, can be any salt of sodium(I), potassium(I), rubidium(I) and/or cesium(I) or precursor thereof which is at least partially soluble in the dispersing liquid, such as the acetate, formate, carbonate, chloride, bromide, sulfate and the like. Sodium(I), potassium(I), rubidium(I) and/or cesium(I) salts containing a decomposable anion such as sodium nitrate, sodium acetate, sodium formate, sodium carbonate, potassium nitrate, potassium acetate, potassium formate, potassium carbonate, etc. are preferred.

Typically, best results are obtained when each of the sources used is chosen to reduce the content of foreign anions and cations in the reaction mix The source of alumina is any material capable of producing alumina, but preferred is a well dispersed, liquid source such as an alumina sol.

The source of boria is a material such as borate or boric acid with pure boric acid being preferred.

Typically, the mole ratios of the various reactants can be varied to produce the solids of this invention.

Specifically, the mole ratios in terms of oxides of the initial reactant concentrations are characterized by the general mixed oxide formula $$(x)M_2O \cdot (y)Al_2O_3 \cdot (z)B_2O_3$$

where M is at least one metallo element selected from Group IA of the Periodic Table having an atomic number from 11 through 55, inclusive, and x, y and z are numbers representing molar amounts of the oxides of the source reagents. Typically, the mole ratios of $M_2O/B_2O_3$, calculated as x/z, are about 0.1 to about 25 and the mole ratios of $Al_2O_3/B_2O_3$, calculated as y/z, can range from about 0.2 up to about 50 or more. For the amorphous solid materials of the present invention the mole ratio of $M_2O/B_2O_3$, calculated as x/z, is in a range of about 0.2 to about 10, preferably about 0.55 to about 3, and the mole ratios of $Al_2O_3/B_2O_3$, calculated as y/z, is in a range of about 2.3 to about 35, preferably about 3 to about 20. For the crystalline solid materials on the present invention the mole ratios of $M_2O/B_2O_3$, calculated as x/z, is in a range of about 0.55 to about 3, preferably about 0.67 to about 2, and the mole ratios of $Al_2O_3/B_2O_3$, calculated as y/z, is in a range of 0.3 up to about 3, preferably about 0.4 to about 2.35.

In somewhat greater detail, a preferred procedure is to dissolve the boria source and disperse the alumina source in water with mixing in a blender for about 3–5 minutes, then adding an aqueous solution of a source of a Group IA metallo element to the blender followed by gelation with a suitable base, preferably aqueous ammonia.

Typically, the pH of the aqueous mixture is less than about 11. If the reaction media is too acid or too basic, the desired solid generally will not form or other contaminating phases are formed in addition to the desired product. To some extent the pH of the reaction mixture controls surface properties of the final calcined solid material. Preferably, the pH of the reaction mixture is in a range from about 4 to about 10, more preferably about 5 to about 9, in order to gel the reaction mixture. If desired, the pH can be adjusted with a base such as ammonia, ethylenediamine, tetramethylammonium hydroxide and the like. Preferred is the use of ammonium hydroxide. The presence of the ammonia as well as other volatile components in the gelled mixture, such as acetate ion, nitrate ion, etc., is advantageous in providing the final calcined solid with sufficiently high surface area and porosity desirable for catalytic reactions.

The gelled mixture is allowed to air dry, usually for about 1–3 days, followed by vacuum drying, typically at a pressure of about 0.3 atmosphere for about 15 to 25 hours at about 80° C. to 150° C. with a nitrogen purge.

In one method aspect of this invention, the produced gel can be formed into beads, cylinders or other suitable shapes of a desired configuration, and then dried. For example, the gel can be dried as a sheet-form material.

In general, the drying step can be carried out at about atmospheric pressure. Alternatively, the drying step can be carried out at a subatmospheric. Preferably, drying is carried out in two stages, a first stage at about atmospheric pressure followed by a second stage at subatmospheric pressure and at a relatively lower temperature, e.g. about 150° C. (about 300° F.) or below. The gel is then dried to a crushable solid state. It is preferred to dry the gel to substantially constant weight Drying can be carried out in ambient atmosphere or in an inert atmosphere, as desired.

When it is desirable to dry the gel as a sheet-form material, the dried gel can be comminuted, such as by crushing, prior to further heat treatment.

Calcination temperature and time are catalyst preparation parameters which can be used to fine-tune catalyst selectivity and activity. Longer calcination times can result in lower initial surface area for the catalyst. The superficially dry mixture is calcined, preferably at a temperature within the range of about 400° to about 1100° C. for a reaction time that is sufficient to affect formation of a crystalline metalloaluminum borate, typically a reaction time within the range of about 2 to about 30 hr. Samples of material can be removed during calcination to check the degree of crystallization and determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removes impurities such as excess boria, without destroying the crystalline material formed, mildly dried for anywhere from a few hours to a few days at varying temperatures, typically about 50° to about 225° C., to form a dry cake which can then be treated as required for its intended use.

The solid materials made by this invention can be admixed with or incorporated within various binders or matrix materials depending upon the intended process use. They are combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, STEROTEX (a powdered vegetable stearine produced by Capital City Products, Co., Columbus, Ohio), or other binders well known in the art.

Advantageously, a crystalline material formed according to this invention is formed or combined with from about 0.005 to about 40 wt% of at least one compound of a metallo element selected from the group consisting of Groups IIA, IIIB, and IVA of the Periodic Table based on the weight of solid material. The Periodic Table is the well known arrangement of chemical elements based on the periodic law and is found in *Webster's Ninth New Collegiate Dictionary*, Merriam-Webster Inc., Springfield, Mass., U.S.A., (1984) at page 874.

Suitable alkaline earth metal (Group IIA), heavy metal (Group IIB) and low melting metal (Group IVA) compounds including rare earth compounds of elements in the lanthanide series and actinide series include the oxides, hydroxides and salts of magnesium, calcium, strontium, barium, lanthanum, cerium, and thorium, such as magnesium hydroxide, magnesium bicarbonate, calcium nitrate, magnesium borate, lanthanium borate, strontium acetate, calcium propionate, calcium maleate, etc. Of these, magnesium, in the form of the oxide or in a form readily convertible to the oxide, is preferred. The solid materials formed according to this invention can be treated with from about 0.005 to 40 wt% dopant based on the weight of the solid material. The metal or metal compound can be dry-blended with the aluminum borate, dissolved in a suitable solvent, preferably water, mixed with the solid material and dried; or aqueous solutions of same can be added to feedstocks going to a reactor containing the solid material catalyst.

The cesium compound is preferably a salt selected from the group consisting of cesium carbonate, cesium hydroxide, cesium fluoride and cesium nitrate, and more preferably is cesium carbonate.

Catalyst compositions of this invention are useful generally in the chemical conversion of organic compounds, particularly hydrocarbon and oxygenated hydrocarbon. In particular, chemical conversion reactions such as production of an alpha, beta-ethylenically unsaturated monocarboxylic acid by condensation of a saturated monocarboxylic acid with formaldehyde.

Particularly useful is the fact that when these solid catalyst compositions are used in liquid- and/or gas-phase processes, the products of chemical conversion are easily separated from the solid catalyst material. Also useful is the fact that when these solid catalyst compositions are used in such fluid-phase processes, the active metallo element components are only slowly extracted, leading to longer catalyst lifetime.

Generally, a process of the present invention for chemical conversion comprises contacting under suitable reaction conditions an organic reactant comprising a saturated monocarboxylic acid and formaldehyde in a fluid-phase, i.e. liquid- and/or vapor-phase, with a heterogeneous catalyst composition comprising a solid material having a chemical composition:

$$(x)M_2O \cdot (y)Al_2O_3 (z)B_2O_3$$

where M is at least one metallo element selected form Group IA of the Periodic Table having an atomic number from 11 through 55, inclusive, and x, y and z are numbers representing molar amounts of the oxides.

Suitable unsaturated monocarboxylic acids include those having an alpha-hydrogen, i.e., a hydrogen atom that is alpha to the carboxyl group of the acid. For example, acids containing from about two to about nine carbon atoms, preferably between about two to about five carbon atoms. Thus, suitable monocarboxylic acids include acetic acid, propionic acid, butyric acid, isovaleric acid, caproic acid, enanthic acid, caprylic acid, pelargonic acid and the like.

Suitable reaction conditions for the reaction of an organic reactant comprising a saturated monocarboxylic acid and formaldehyde include the use of elevated temperatures. Typically, a temperature in a range from about 200° C. to about 400° C., preferably from about 250° C. to about 375° C. is contemplated for the condensation processes of this invention. Operating pressures in a range from about 1 to about 10 atmospheres are generally useful, however, higher pressures may be employed if desired. The concentration of reactants employed is varied over a range from 0.3 to about 3 moles of monocarboxylic acid to formaldehyde, preferably from about 0.5 to about 2 moles of monocarboxylic acid to formaldehyde. A weight hourly space velocity in a range from about 0.5 to about 10 $hr^{-1}$, preferably from about 1 to about 5 $hr^{-1}$, may be utilized.

The catalyst of the present invention is particularly well-suited for the gas-phase synthesis of methacrylic acid (MA) via condensation of formaldehyde (FA) with propionic acid (PA). The catalyst of the present invention catalytically induces this condensation reaction.

In a preferred embodiment of the process of this invention, the heterogeneous catalyst comprises amorphous solid material having a surface area of at least 20 $m^2/g$. In an especially preferred embodiment of this process, M is selected from the group potassium, rubidium and cesium.

In another preferred embodiment of the processes of this invention, the heterogeneous catalyst comprises a crystalline $M_2Al_2B_2O_7$, where M is at least one metallo element selected form Group IA of the Periodic Table having an atomic number from 11 through 37, inclusive, having an X-ray diffraction pattern comprising significant lines substantially as described in Table I. In an especially preferred embodiment of this process M is selected from the group sodium, potassium, and rubidium.

The following examples will serve to illustrate certain specific embodiments of the herein disclosed invention. These examples should not, however, be construed as limiting the scope of the novel invention, as there are many variations which may be made thereon without departing from the spirit of the disclosed invention, as those of skill in the art will recognize.

For Example, the vapor-phase condensation reaction takes place in a reactor suitable for effecting desired heterogeneous catalysis. The reactor effluent commonly includes not only the desired synthesis product, MA, and water as a co-product of the desired condensation reaction, but also unreacted PA and FA, a variety of organic by-products and certain relatively volatile gases as well. The thus-synthesized MA can be separated from the unconverted PA and FA reactants and the above-identified co-product and by-products, then esterified with a suitable $C_1$ to $C_4$ aliphatic alcohol such as methanol (MeOH), and thereafter can be purified to obtain a polymer-grade ester such as methyl methacrylate (MMA).

In the ensuing detailed description, certain terms will be utilized for purposes of conciseness, and for purposes of elucidating the features and advantages of the present invention. These terms are defined hereinbelow.

The term "activity of a catalyst" as used herein means the relative ease or difficulty of the catalyst at a given temperature to effect chemical conversion of the reactants to the desired product or products The term "surface area" as used herein means the areas as determined utilizing the well-known BET nitrogen desorption method. [See, e.g., S. Brunauer et al., *J.A.C.S.*, 60, 309, (1938).]

The term "catalyst" as used herein broadly means a substance which increases the rate at which a thermodynamically-allowable chemical reaction takes place. Typically, relatively small percentages of catalyst markedly affect the rate of a given chemical reaction.

The term "calcining" as used herein means subjecting dried material to a temperature of at least about 250° C. (about 480° F ).

The term "drying" as used herein means subjecting the material to be dried to a temperature of no more than about 250° C. (about 480° F.).

The term "WHSV" as used herein means weight hourly space velocity, and is expressed as grams of feed per gram of catalyst per hour.

Additional definitions include the following equations:

Yield (Y), based on propionic acid:

$$\% \ Y(PA) = \frac{\text{mols of } MA \text{ produced}}{\text{mols of } PA \text{ in feed}} \times 100$$

Yield (Y), based on formaldehyde:

$$\% \ Y(FA) = \frac{\text{mols of } MA \text{ produced}}{\text{mols of } FA \text{ in feed}} \times 100$$

Methacrylic acid selectivity (S), based on propionic acid:

$$\% \ S \ (PA) = \frac{\text{mols of } MA \text{ produced}}{\text{mols of } PA \text{ reacted}} \times 100$$

Methacrylic acid selectivity (S), based on formaldehyde:

$$\% \ S \ (FA) = \frac{\text{mols of } MA \text{ produced}}{\text{mols of } FA \text{ reacted}} \times 100$$

Conversion (C):

$$\% \ C = \frac{\% \ Y}{\% \ S} \times 100$$

Similar terminology will be utilized to describe the yield, selectivity and conversion of the organic by-products when the performance of the present catalyst is discussed.

In the examples appearing below, the following conditions were maintained, and the following equipment and procedures were used, unless otherwise indicated.

Reagent-grade trioxane was used as the FA source; however, in the conversion of PA with FA in the presence of the catalyst of this invention to synthesize MA, any suitable source of formaldehyde can be used, such as formalin, paraformaldehyde, methanolic formaldehyde, substantially anhydrous formaldehyde, and the like.

A laboratory minireactor was used to determine the MA-synthesis performance of each catalyst. All experimental determinations or runs were conducted at a PA/FA mole ratio of about 3/2. The minireactor comprised an elongated 12.7 mm (millimeter) O.D. quartz tube having an externally controllable thermowell longitudinally disposed in, and along the longitudinal axis of, the quartz tube. Catalyst to be tested for MA-synthesis performance-determination purposes was placed in the quartz tube and about the thermowell, forming an annular catalyst bed. Each bed of catalyst contained about 2 to about 3 grams of catalyst having a particle size of about 20 to about 40 mesh (U.S. Sieve). A spun quartz plug supported each catalyst bed.

The trioxane was thermally cracked by passing the feed through a hot reactor zone, heated to a temperature of about 390° C. (about 735° F.) to about 440° C. (about 825° F.), and located above the catalyst zone, prior to passing the feed through the catalyst bed.

The vapor-phase synthesis of methacrylic acid from propionic acid commonly produces coke, which is observed to deposit on the catalyst surface. Such coke deposits are usually removed from the catalyst by burning off with oxygen utilizing dilute air. Typically, catalyst decoking is effected whenever MA-synthesis performance of the catalyst falls below a predetermined criterion, such as a given value of percent conversion of PA to MA.

Initial performance studies were generally carried out by subjecting each investigated catalyst to appropriate MA-synthesis conditions for about 30 minutes prior to collecting the desired number of aliquot samples for analytical purposes, and thereafter decoking with air before removing additional aliquot samples. This particular catalyst decoking procedure was utilized to reduce the likelihood of a variable build-up of coke upon the catalyst, which might affect evaluation of catalyst performance.

General sampling procedures, for analytical purposes, included collection of about 10 to about 25 grams of the reactor effluent in a tared U-tube, or Erlenmeyer-type receiver containing about 10 to about 25 grams of isopropanol at room temperature (RT), i.e. about 25° C. Reactor effluent samples were thereafter analyzed via gas chromatography (GC), employing internal-standard techniques. That is, the GC response for each of the organic components in the minireactor effluent was based upon the known response of the GC to an internal standard added to the sample. Actual PA titrations indicated that the propionic acid used in the feed was about 99.6 to about 99.9% pure.

Each of the Tables appearing below presents the MA-synthesis performance data of a single catalyst over a period of time, unless stated otherwise.

EXAMPLE 1

Into a WARING high speed mechanical blender were placed 261.5 g of a 7.8% alumina sol (0.200 mol), 27.64 g potassium carbonate (0.200 mol) dissolved in 32 mL distilled water, and 32.96 g boric acid (0.533 mol) dissolved in 178 mL hot distilled water. The materials were blended together. Ammonium hydroxide, 30 mL, was blended into the mixture to produce a paste-like gel. The mixture was placed onto a 35×45 cm plastic tray for air drying. After air drying for three days, the material weighed 79.7 g. This material was placed into a PYREX glass dish and vacuum dried at 120° C. and 0.3 atm pressure, with a nitrogen purge. After 17 hours, the solid weighed 68.3 g.

A portion of the sample (18.1 g) placed in an alumina tray and calcined according to the following program:

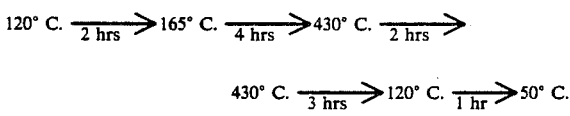

The resulting product weighed 15.1 g. The product was analyzed by powder XRD and BET surface analysis. The BET desorption surface area was determined to be 27 m²/g. The powder XRD analysis showed this product had no apparent crystalline form.

EXAMPLES 2-3

Into a WARING high speed mechanical blender were placed 348.72 g of a pHF alumina sol which was 7.8% Al$_2$O$_3$ by weight (0.27 mol), 4.61 g of K (0.033 mol) dissolved in 5 mL of hot distilled water, and 4.12 g H (0.066 mol) dissolved in 22 mL of hot distilled water. The mixture was stirred into a thick gel, which had a pH of 5. Addition of 25 mL of concentrated ammonium hydroxide resulted, upon blending, in a thick paste-like material which had a pH of 10. The mixture was spread into a 35×45 cm tray to air dry. After three days, the resulting dry chunks had a mass of 55.6 g. The chunks were placed in a 100×50 mm Pyrex dish and dried in at vacuum oven at 120° C. and 0.3 atm pressure, with a nitrogen purge, for 17 hours. The product then had a mass of 45.4 g. A portion (18.1 g) of the product was placed in an alumina tray and calcined according to the following program:

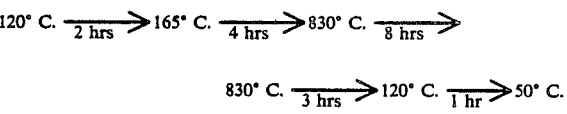

The resulting product weighed 13.8 g, and was labeled Example 2. This product was analyzed by powder XRD and BET surface analysis. The BET desorption surface area was determined to be 257 m²/g. The powder XRD analysis showed this product had no apparent crystalline form. A second 18.1 g sample is calcined as follows:

$$120° C. \xrightarrow{2 \text{ hrs}} 165° C. \xrightarrow{4 \text{ hrs}} 425° C. \xrightarrow{8 \text{ hrs}}$$

$$425° C. \xrightarrow{3 \text{ hrs}} 120° C. \xrightarrow{1 \text{ hr}} 50° C.$$

The material weighed 12.0 g and was labeled Example 3. This product was analyzed by powder XRD which showed this product had no apparent crystalline form.

EXAMPLES 4–6

Into a WARING high speed mechanical blender were placed 348.7 g of a PHF alumina sol which contained 7.8% Al₂O₃ by weight (0.27 mol), 10.87 g of Cs₂CO₃ (0.033 mol) dissolved in 12 mL hot distilled water, and 4.12 g H₃BO₃ (0.066 mol) dissolved in 21 mL hot distilled water. The resulting mixture was a white gel which had a pH of 5.8. Ammonium hydroxide, 59 mL, was added and the mixture blended. The resulting paste had a pH of 10.6. This material was spread onto a 35×45 cm plastic tray and air dried. The resulting weight was 64.08 g. The air dried material was placed in a Pyrex dish and vacuum dried at 120° C. and 0.3 atm pressure with a nitrogen purge. The dry solid weighed 49.7 g.

A portion (18.1 g) of this solid was calcined according to the same program as used in Example 1 hereinabove resulting in a final catalyst weight of 13.7 g. This calcined material was labeled Example 4. This product was analyzed by powder XRD and BET surface analysis. The BET desorption surface area was determined to be 100 m²/g. The powder XRD analysis showed this product had no apparent crystalline form.

A second portion (18.1 g) was calcined according to the following program:

$$120° C. \xrightarrow{2 \text{ hrs}} 165° C. \xrightarrow{4 \text{ hrs}} 600° C. \xrightarrow{8 \text{ hrs}}$$

$$600° C. \xrightarrow{3 \text{ hrs}} 120° C. \xrightarrow{1 \text{ hr}} 50° C.$$

Calcination of this sample yielded 13.4 g of material which was labeled Example 5. This product was analyzed by powder XRD and BET surface analysis. The BET desorption surface area was determined to be 193 m²/g. The powder XRD analysis showed this product had no apparent crystalline form.

A third sample (9.05 g) was calcined according to the following program:

$$120° C. \xrightarrow{2 \text{ hrs}} 165° C. \xrightarrow{4 \text{ hrs}} 420° C. \xrightarrow{8 \text{ hrs}}$$

$$420° C. \xrightarrow{3 \text{ hrs}} 120° C. \xrightarrow{1 \text{ hr}} 50° C.$$

Calcination of this sample yielded 6.79 g of material which was labeled Example 6. This product was analyzed by powder XRD and BET surface analysis. The BET desorption surface area was determined to be 264 m²/g. The powder XRD analysis showed this product had no apparent crystalline form.

EXAMPLES 7–8

Into a WARING high speed mechanical blender were placed 506.2 g of a PHF alumina sol which was 7.56% alumina by weight (0.375 mol), 4.07 g Cs₂CO₃ (0.0125 mol) dissolved in 5 mL distilled water, and 9.27 g (0.150 mol) H₃BO₃ dissolved in 46 mL hot distilled water. The combined materials were blended, resulting in a thin liquid-like mixture which had a pH of 4.6. Ammonium hydroxide, 100 mL, was blended into the mixture to adjust the pH to 10.4. The resulting mixture was a thick white gel. The gel was spread onto a 35×45 cm plastic tray to air dry. The resulting mass was 76.7 g. The solids were placed into a PYREX glass dish and dried in a vacuum oven at 120° C. and 0.3 atm pressure, with a nitrogen gas purge. The solids then had a mass of 62.6 g.

A portion (18.1 g) was calcined in an alumina tray according to the same program as Example 2, resulting in a final product weighing 13.3 g. This sample was labeled Example 7. This product was analyzed by powder XRD and BET surface analysis. The BET desorption surface area was determined to be 144 m²/g. The powder XRD analysis showed some weak lines indicating no apparent crystalline form.

A second portion (18.1 g) is calcined according to the following program:

$$120° C. \xrightarrow{2 \text{ hrs}} 165° C. \xrightarrow{4 \text{ hrs}} 780° C. \xrightarrow{8 \text{ hrs}}$$

$$780° C. \xrightarrow{3 \text{ hrs}} 120° C. \xrightarrow{1 \text{ hr}} 50° C.$$

Calcination of this sample yielded 12.7 g of material which was labeled Example 8. This product was analyzed by powder XRD and BET surface analysis. The BET desorption surface area was determined to be 175 m²/g. The powder XRD analysis showed some weak lines indicating no apparent crystalline form.

EXAMPLES 9–12

Methacrylic Acid Synthesis a. General procedure

Catalyst testing runs were carried out in 12.7 mm OD Quartz tubes heated by triple-zone Thermacraft tube furnaces. The annular catalyst bed, formed by the use of a 5 mm central thermowell, typically consisted of 2.55 g of 18–40 mesh catalyst supported by a spun quartz plug. Feed (a 3:2 molar ratio of propionic acid (PA) and formaldehyde (FA) as trioxane) was delivered and measured volumetrically by means of either an Eldex micrometering pump or a laboratory FMI pump with micrometer flow adjustment. Trioxane was cracked thermally to produce gaseous FA by passing the feed through a hot reactor zone (400°–420° C.) located above the catalyst zone. Initial performance studies were typically carried out by running the catalyst for about one-half hour prior to collection of an analytical sample, and decoking the catalyst with air before the next sample. The sampling procedure consisted of collection of approximately 10–25 g of reactor effluent in a tared U-tube or flask containing a comparable amount of isopropanol (IPA) at room temperature. Reactor effluent samples were analyzed using an internal standard GC method. All results reported are based on PA.

b. Results of Catalyst Testing

The materials of Examples 1 and 2, containing potassium, aluminum, boron and oxygen, and of Examples 5 and 8, containing cesium, aluminum, boron and oxygen, were tested. Test results are set out below:

| Methacrylic Acid and Synthesis Using Potassium-containing Catalysts | | | | |
|---|---|---|---|---|
| Example | WHSV | T(C) | % PAC | % PAS |
| Catalyst of Example 1 | | | | |
| 9 | 1.74 | 356 | 40.5 | 22 |
| 9 | 1.68 | 344 | 26.1 | 28 |
| 9 | 1.52 | 332 | 26.6 | 41 |
| 9 | 1.53 | 320 | 16.7 | 50 |
| 9 | 1.53 | 309 | 19.1 | 56 |
| Catalyst of Example 2 | | | | |
| 10 | 1.58 | 352 | 46.0 | 28 |
| 10 | 1.55 | 335 | 34.2 | 41 |
| 10 | 1.54 | 317 | 33.9 | 46 |
| 10 | 1.51 | 306 | 27.8 | 44 |
| 10 | 1.49 | 293 | 26.9 | 54 |
| 10 | 1.50 | 282 | 27.9 | 51 |
| 10 | 1.53 | 269 | 20.5 | 52 |
| 10 | 1.51 | 260 | 17.2 | 58 |

% PAC = % PA conversion
% PAS = % PA selectivity to MA
WHSV = Weight Hourly Space Velocity = g feed/((g cat)°hr)
T(C) = Temperature in degrees C.

| Methacrylic Acid Synthesis Using Cesium-containing Catalysts | | | | |
|---|---|---|---|---|
| Example | WHSV | T(C) | % PAC | % PAS |
| Catalyst of Example 5 | | | | |
| 11 | 1.45 | 281 | 23.4 | 51 |
| 11 | 1.45 | 280 | 22.9 | 48 |
| 11 | 1.45 | 293 | 25.5 | 49 |
| 11 | 1.45 | 303 | 27.7 | 45 |
| 11 | 1.46 | 319 | 31.4 | 41 |
| Catalyst of Example 8 | | | | |
| 12 | 1.59 | 315 | 17.4 | 62 |
| 12 | 1.47 | 303 | 15.0 | 53 |
| 12 | 1.57 | 291 | 13.5 | 52 |
| 12 | 1.45 | 337 | 21.2 | 63 |
| 12 | 1.44 | 349 | 25.4 | 57 |
| 12 | 1.48 | 361 | 29.3 | 52 |

% PAC = % PA conversion
% PAS = % PA selectivity to MA
WHSV = Weight Hourly Space Velocity = g feed/((g cat)°hr)
T(C) = Temperature in degrees C.

EXAMPLE 13

Into a WARING high speed mechanical blender were placed potassium carbonate (33.2g, 0.24 mol) dissolved in 38 mL deionized water, boric acid (44.5 g, 0.72 mol) dissolved in 240 ml warm deionized water, and alumina (261.5 g of a 7.8% alumina sol, 0.20 mol). The mixture was blended, followed by addition of 49 mL ammonium hydroxide. Blending was continued for several minutes on both low and high settings The resulting gel was allowed to air dry on a 35 cm×45 cm plastic tray. The material was vacuum dried at 113° C. and 0.3 atm with a nitrogen purge for 17 hrs. The product weighed 81.1 g. An 18.1 g portion was calcined using the following program:

$$120° C. \xrightarrow{2 \text{ hrs}} 165° C. \xrightarrow{4 \text{ hrs}} 830° C. \xrightarrow{8 \text{ hrs}}$$

$$830° C. \xrightarrow{3 \text{ hrs}} 120° C. \longrightarrow RT$$

The resulting product weighed 13.5 g. The product was analyzed by powder XRD, ICP elemental analysis and BET surface analysis. Elemental analysis showed 26.2% potassium, 16.0% aluminum and 11.3% boron. The BET desorption surface area was determined to be 9 m²/g. The powder XRD is set out below:

| XRD Lines for $K_2Al_2B_2O_7$ | |
|---|---|
| Interplanar Spacing d, Å[1] | Assigned Strength[2] |
| 5.576 | VW |
| 4.280 | W |
| 4.230 | W |
| 3.674 | VW |
| 3.3953 | W |
| 3.0081 | VS |
| 2.6598 | W |
| 2.4712 | M |
| 2.3718 | W |
| 2.1399 | W |
| 2.1333 | W |
| 2.1146 | M |
| 1.9974 | VW |
| 1.9875 | VW |
| 1.9097 | VW |
| 1.8961 | VW |
| 1.8584 | VW |
| 1.6671 | VW |
| 1.6176 | VW |
| 1.6068 | VW |
| 1.5890 | VW |
| 1.5390 | VW |
| 1.5109 | W |
| 1.5043 | VW |
| 1.4483 | VW |
| 1.4267 | VW |

[1]Angstroms
[2]VW = very weak; W = weak; M = medium; S = strong; VS = very strong

EXAMPLE 14

Into a WARING high speed mechanical blender were placed 261.5 g of a 7.8% alumina sol (0.200 mol), 27.64 g potassium carbonate (0.200 mol) dissolved in 32 mL distilled water, and 32.96 g boric acid (0.533 mol) dissolved in 178 mL hot distilled water. The materials were blended together. Ammonium hydroxide, 30 mL, was blended into the mixture to produce a paste-like gel. The mixture was placed onto a 35×45 cm plastic tray for air drying. After air drying for three days, the material weighed 79.7 g. The solids were placed into a PYREX glass dish and vacuum dried at 120° C. and 0.3 atm pressure, with a nitrogen purge. After 17 hours, the solids weighed 68.3 g.

A portion of the sample (18.1 g) was placed in an alumina tray and calcined according to the following program:

$$120° C. \xrightarrow{2 \text{ hrs}} 165° C. \xrightarrow{4 \text{ hrs}} 830° C. \xrightarrow{8 \text{ hrs}}$$

$$830° C. \xrightarrow{3 \text{ hrs}} 120° C. \xrightarrow{1 \text{ hr}} 50° C.$$

The resulting product weighed 13.9 g. The product was analyzed by powder XRD and BET surface analysis. The powder XRD pattern comprised significant lines substantially as described in Table I. The BET desorption surface area was determined to be 8 m²/g.

EXAMPLE 15

Into a WARING high speed mechanical blender were placed potassium carbonate (40.0 g, 0.29 mol) dissolved in 40 mL of deionized water, boric acid (18.6 g, 0.30 mol) dissolved in 193 mL warm deionized water, and aluminum nitrate-9 H₂O (185 g, 0.49 mol) dissolved in 300 mL deionized water. Considerable evolution of CO₂ was observed. After mixing at a low speed, 51 mL of ammonium hydroxide was added, and the mixture was blended. Addition of a further 46 mL of ammonium hydroxide was accompanied by blending at high settings for about 5-10 minutes total time. The smooth white gel was spread on a 35×45 cm plastic tray and allowed to air dry. The entire mass was placed in a vacuum oven overnight at 105° C. and 0.3 atm with a nitrogen flow. The yield was 142.8 g. A portion of the material was calcined using the following temperature program:

$$25°\text{ C.} \xrightarrow{2 \text{ hrs}} 165°\text{ C.} \xrightarrow{4 \text{ hrs}} 830°\text{ C.} \xrightarrow{8 \text{ hrs}}$$

$$830°\text{ C.} \longrightarrow \text{RT}$$

The product was analyzed by powder XRD and BET surface analysis. The powder XRD pattern comprised significant lines substantially as described in Table I. The BET desorption surface area was determined to be 4 m²/g.

EXAMPLE 16

Into a WARING high speed mechanical blender were placed potassium carbonate (22.8 g, 0.165 mol) dissolved in 65 mL deionized water, boric acid (20.4 g, 0.331 mol) dissolved in 150 mL warm deionized water, and alumina (215.8 g of a 7.8% Al₂O₃ sol, 0.165 mol) and blended. Addition of 110 mL of ammonium hydroxide and continued agitation resulted in the formation of a gel. The gel was placed onto a 35 cm×45 cm tray for air drying. The material was placed in a vacuum oven at 105° C. for 17 hrs in 0.3 atm with a nitrogen purge. The resultant weight was 53.0 g. A portion (37.7 g) of the material was calcined with the following program:

$$120°\text{ C.} \xrightarrow{2 \text{ hrs}} 165°\text{ C.} \xrightarrow{4 \text{ hrs}} 830°\text{ C.} \xrightarrow{8 \text{ hrs}}$$

$$830°\text{ C.} \xrightarrow{3 \text{ hrs}} 120°\text{ C.} \longrightarrow \text{RT}$$

The resulting product weighed 28.6 g. The product was analyzed by powder XRD, ICP elemental analysis and BET surface analysis. The powder XRD pattern comprised significant lines substantially as described in Table I. Elemental analysis showed 28.0% potassium, 19.7% aluminum and 7.6% boron. The BET desorption surface area was determined to be 2 m²/g.

Into a WARING high speed mechanical blender were placed potassium carbonate (13.8 g, 0.10 mol) dissolved in 15 mL warm deionized water, boric acid (12.4 g, 0.20 mol) dissolved in 95 mL deionized water, and alumina (392.3 g of a 7.8% alumina sol, 0.30 mol). After mixing the ingredients, 56 mL ammonium hydroxide was added, with low and high mixing. The resulting gel was spread onto a 35 cm×45 cm tray and air dried. This material was vacuum dried at 105° C. and 0.3 atm in a nitrogen purge for 17 hrs to give 64.8 g of material. A portion of the material was calcined with the following program:

$$120°\text{ C.} \xrightarrow{2 \text{ hrs}} 165°\text{ C.} \xrightarrow{4 \text{ hrs}} 830°\text{ C.} \xrightarrow{8 \text{ hrs}}$$

$$830°\text{ C.} \xrightarrow{3 \text{ hrs}} 120°\text{ C.} \longrightarrow \text{RT}$$

The product was analyzed by powder XRD, ICP elemental analysis and BET surface analysis. The powder XRD pattern comprised significant lines substantially as described in Table I. Elemental analysis showed 22.1% potassium, 16.1% aluminum and 12.7% boron. The BET desorption surface area was determined to be 5 m²/g.

EXAMPLE 18

Into a WARING high speed mechanical blender were placed potassium carbonate (27.6 g, 0.20 mol) dissolved in 32 mL warm deionized water, boric acid (39.6 g, 0.64 mol) dissolved in 214 mL deionized water, and alumina (366.2 g of a 7.8% alumina sol, 0.28 mol). After mixing the ingredients, 24 mL ammonium hydroxide was added, with low and high mixing. The resulting gel, which weighed 102.4 g, was spread onto a 35 cm×45 cm tray and air dried. This material, which weighed 87.5 g, was vacuum dried at 113° C. and 0.3 atm in a nitrogen purge for 17 hrs. to give 81.1 g of material. A portion (18.1 g) of the material was calcined with the following program:

$$120°\text{ C.} \xrightarrow{2 \text{ hrs}} 165°\text{ C.} \xrightarrow{4 \text{ hrs}} 830°\text{ C.} \xrightarrow{8 \text{ hrs}}$$

$$830°\text{ C.} \xrightarrow{3 \text{ hrs}} 120°\text{ C.} \longrightarrow \text{RT}$$

The resulting product weighed 13.2 g. The product was analyzed by powder XRD, ICP elemental analysis and BET surface analysis. The powder XRD pattern comprised significant lines substantially as described in Table I. Elemental analysis showed 22.5% potassium, 21.6% aluminum and 9.8% boron. The BET desorption surface area was

EXAMPLE 19

Into a WARING high speed mechanical blender were placed potassium nitrate (60.7 g, 0.60 mol) dissolved in 120 mL warm deionized water, boric acid (49.4 g, 0.80 mol) dissolved in 270 mL deionized water, and alumina (392.3 g of a 7.8% alumina sol, 0.30 mol). A thick gel was formed on blending. No ammonium hydroxide was added. The resulting gel was air dried. A portion of this material which weighed 75.0 g was vacuum dried at 120° C. and 0.3 atm in a nitrogen purge for 17 hrs to give 54.8 g of material. A portion (17.4 g) of the material was calcined with the following program:

$$120°\text{ C.} \xrightarrow{2 \text{ hrs}} 165°\text{ C.} \xrightarrow{4 \text{ hrs}} 830°\text{ C.} \xrightarrow{8 \text{ hrs}}$$

$$830°\text{ C.} \xrightarrow{1 \text{ hr}} 960°\text{ C.} \xrightarrow{4 \text{ hrs}} 960°\text{ C.} \xrightarrow{3 \text{ hrs}}$$

120° C. ⟶ RT

The resulting product weighed 9.2 g. The product was analyzed by powder XRD and BET surface analysis. The powder XRD pattern comprised significant lines substantially as described in Table I. The BET desorption surface area was determined to be 0.02 m$_2$/g.

What is claimed is:

1. A solid material consisting essentially of aluminum, boron, oxygen and at least one metallo element selected from Group IA of the Periodic Table having an atomic number from 11 through 55, inclusive, wherein the solid material is amorphous and has a surface area of at least 20 m$^2$g.

2. The solid material of claim 1 with a binder.

3. The composition of claim 1 wherein one metallo element selected from Group IA of the Periodic Table is potassium.

4. An amorphous solid material consisting essentially of aluminum, boron, oxygen and at least one metallo element selected from Group IA of the Periodic Table having an atomic number from 11 through 55, inclusive made by a process which comprises dispersing in a liquid medium a source of alumina, a source of boria, and a source of at least one metallo element ion selected from the group consisting of sodium(I) ions, potassium(I) ions, rubidium(I) ions and cesium(I) ions, at a molar ratio of the source of metallo element ions to the source of boria, in terms of oxides calculated as (Na$_2$O+K$_2$O+Rb$_2$O+Cs$_2$O)/B$_2$O$_3$, in a range from about 0.1 to about 25, and the molar ratio of the source of alumina to the source of boria, in terms of oxides calculated as Al$_2$O$_3$/B$_2$O$_3$, in a range from about 0.2 to about 50, removing substantially all the liquid to form a superficially dry solid, and calcining the superficially dry solid at a temperature in a range from about 400° C. to about 1100° C.

5. The composition of claim 4 wherein the molar ratio of the source of metallo element ions to the source of boria, in terms of oxides calculated as (Na$_2$O+K$_2$O+Rb$_2$O+Cs$_2$O)/B$_2$O$_3$, is in a range from about 0.2 to about 10, and the molar ratio of the source of alumina to the source of boria, in terms of oxides calculated as Al$_2$O$_3$/B$_2$O$_3$, is in a range from about 2.3 to about 35.

6. The composition of claim 4 with a binder.

7. The composition of claim 4 wherein one metallo element selected from Group IA of the Periodic Table is potassium.

* * * * *

UNITED STATES PATENT AND TRADEMARK OFFICE
CERTIFICATE OF CORRECTION

PATENT NO. : 5,104,845            Page 1 of 4

DATED : April 14, 1988

INVENTOR(S) : Ruth A. Montag, et al

It is certified that error appears in the above-identified patent and that said Letters Patent is hereby corrected as shown below:

| Column | Line(s) | |
|---|---|---|
| 1 | 28 | reads "support McArthur" and should read --support. McArthur-- |
| 1 | 33-34 | reads "compound McArthur" and should read --compound. McArthur-- |
| 1 | 41-42 | reads "salt-impregnated In U.S. Pat No." and should read --salt-impregnated support to convert the impregnated salt to the active catalytic form. McArthur neither discloses nor suggests a mixed oxide composition of a metallo element, aluminum and boron. In U.S. Pat. No.-- |
| 1 | 67 | reads "Al Satek" and should read --$Al_4B_2O_9$. Satek-- |
| 2 | 31 | reads "reported Boroaluminates" should read --reported. Boroaluminates-- |

UNITED STATES PATENT AND TRADEMARK OFFICE
CERTIFICATE OF CORRECTION

PATENT NO. : 5,104,845

DATED : April 14, 1988

INVENTOR(S) : Ruth A. Montag, et al

It is certified that error appears in the above-identified patent and that said Letters Patent is hereby corrected as shown below:

| Column | Line(s) | |
|---|---|---|
| 2 | 58 | reads "polymers The MMA-type" should read --polymers. The MMA-type-- |
| 2 | 60 | reads "properties Typical" should read --properties. Typical-- |
| 3 | 9 | reads "products Also" should read --products. Also-- |
| 3 | 15 | reads "purposes Reaction" should read --purposes. Reaction-- |
| 6 | 26 | reads "cesium hydrogen chloride (CsCl)," should read --cesium hydrogen carbonate ($CsHCO_3$), cesium chlorate ($CsClO_3$), cesium chloride (CsCl)-- |
| 6 | 42 | reads "utilized More" should read --utilized. More-- |

UNITED STATES PATENT AND TRADEMARK OFFICE
CERTIFICATE OF CORRECTION

PATENT NO. : 5,104,845

DATED : April 14, 1988

INVENTOR(S) : Ruth A. Montag, et al

It is certified that error appears in the above-identified patent and that said Letters Patent is hereby corrected as shown below:

| Column | Line(s) | |
|---|---|---|
| 6 | 64-65 | reads "of this Invention. Specifically" should read --of this Invention. Specifically-- |
| 9 | 25 | reads "$(x)M_2O \cdot (y)Al_2O_3(z)B_2O_3$" should read --$(x)M_2O \cdot (y)Al_2O_3 \cdot (z)B_2O_3$-- |
| 12 | 44 | reads "pHF" should read --PHF-- |
| 12 | 45-46 | reads "K(0.033mol)" should read --$K_2CO_3$(0.033 mol)-- |
| 12 | 46-47 | reads "4.12g H(0.066 mol)" should read --4.12g $H_3BO_3$(0.066 mol)-- |
| 15 | 59 | reads "setting The" should read --settings. The-- |

UNITED STATES PATENT AND TRADEMARK OFFICE
CERTIFICATE OF CORRECTION

PATENT NO. : 5,104,845

DATED : April 14, 1988

INVENTOR(S) : Ruth A. Montag, et al

It is certified that error appears in the above-identified patent and that said Letters Patent is hereby corrected as shown below:

| Column | Line | |
|---|---|---|
| 17 | 47 | reads $120°C \xrightarrow{2hrs} 165°C \xrightarrow{4hrs} 830°C \xrightarrow{8hrs} 830°C \xrightarrow{3hrs} 120°C \rightarrow RT$ <br><br> should read <br> $--120°C \xrightarrow{2hrs} 165°C \xrightarrow{4hrs} 830°C \xrightarrow{8hrs} 830°C \xrightarrow{4hrs} 120°C \rightarrow RT$ |
| 17 | 60 | reads "determined to be $2m^2/g$. <br> Into a WARING high" should read --determined to be $2m^2/g$. <br>     Example 17 <br><br> Into a WARING high-- |
| 18 | 48 | reads "The BET desorption surface area was <br>     Example 19" should read --The BET desorption surface area was determined to be $9m^2/g$. <br>     Example 19-- |

Signed and Sealed this

Thirteenth Day of July, 1993

*Attest:*

MICHAEL K. KIRK

*Attesting Officer*      *Acting Commissioner of Patents and Trademarks*